US012788296B2

(12) United States Patent
Ramasamy

(10) Patent No.: US 12,788,296 B2
(45) Date of Patent: Nov. 10, 2026

(54) WEARABLE MULTI-MODAL SENSING DEVICE FOR REAL-TIME NEUROLOGICAL MONITORING AND DISORDER DETECTION

(71) Applicant: Aishwarya Ramasamy, Louisville, KY (US)

(72) Inventor: Aishwarya Ramasamy, Louisville, KY (US)

(73) Assignee: Aishwarya Ramasamy, Louisville, KY (US)

( * ) Notice: Subject to any disclaimer, the term of this patent is extended or adjusted under 35 U.S.C. 154(b) by 101 days.

(21) Appl. No.: 19/012,776

(22) Filed: Jan. 7, 2025

(65) Prior Publication Data

US 2026/0191451 A1 Jul. 9, 2026

(51) Int. Cl.

| | |
|---|---|
| ***A61B 5/256*** | (2021.01) |
| ***A61B 5/00*** | (2006.01) |
| ***A61B 5/0205*** | (2006.01) |
| ***A61B 5/291*** | (2021.01) |

(Continued)

(52) U.S. Cl.

CPC ............ *A61B 5/256* (2021.01); *A61B 5/0006* (2013.01); *A61B 5/0022* (2013.01); *A61B 5/0205* (2013.01); *A61B 5/291* (2021.01); *A61B 5/372* (2021.01); *A61B 5/6803* (2013.01); *A61B 5/0077* (2013.01); *A61B 5/14542* (2013.01); *A61B 5/4094* (2013.01); *A61B 5/4818* (2013.01); *A61B 2560/0443* (2013.01); *A61B 2562/063* (2013.01)

(58) Field of Classification Search

CPC ....... A61B 5/256; A61B 5/372; A61B 5/4094; A61B 5/4818; A61B 2560/0443; A61B 5/6803; A61B 5/681; A61B 5/6814; A61B 5/6824; A61B 5/6829

See application file for complete search history.

(56) References Cited

U.S. PATENT DOCUMENTS

2005/0240086 A1* 10/2005 Akay .................. A61B 5/1124 600/595
2015/0125832 A1* 5/2015 Tran ......................... G09B 5/00 434/127
2017/0020444 A1* 1/2017 Lurie ....................... A61B 5/74

(Continued)

*Primary Examiner* — Eric D. Bertram

(57) ABSTRACT

A wearable neurological monitoring device is disclosed, comprising a modular structure configurable as a headband, wristband, or anklet for placement on various body parts. The device includes a plurality of physiological sensors operable to detect signals such as brain activity, motion, temperature, humidity, sound patterns, and muscle tension, enabling real-time monitoring and diagnosis of neurological conditions like epilepsy, Parkinson's disease, sleep apnea, and stress. A processing unit analyzes sensor data using predefined algorithms to identify patterns indicative of neurological abnormalities and generates diagnostic outputs. The device features a communication module for wireless data transmission to external devices, facilitating remote monitoring and diagnostics. Designed for comfort, adaptability, and energy efficiency, the device supports modular sensor configurations, secure data handling, and compatibility with mobile applications and cloud platforms. This invention addresses the need for accessible, low-cost, and non-invasive neurological health monitoring solutions for diverse environments and populations.

9 Claims, 14 Drawing Sheets

(51) Int. Cl.

| | |
|---|---|
| ***A61B 5/372*** | (2021.01) |
| *A61B 5/145* | (2006.01) |

(56) References Cited

U.S. PATENT DOCUMENTS

| | | | | |
|---|---|---|---|---|
| 2018/0303190 | A1* | 10/2018 | Calilung | A42B 3/227 |
| 2019/0113774 | A1* | 4/2019 | Anderson | G02B 27/017 |
| 2021/0169417 | A1* | 6/2021 | Burton | A61B 5/02055 |
| 2021/0282701 | A1* | 9/2021 | Chan | A61B 5/4094 |
| 2022/0071547 | A1* | 3/2022 | Revels | A61B 5/372 |
| 2022/0354373 | A1* | 11/2022 | Monson | A61B 5/0205 |
| 2023/0031613 | A1* | 2/2023 | Fleury | A61B 5/01 |
| 2024/0341652 | A1* | 10/2024 | Connor | A61B 5/375 |

* cited by examiner

| Sl. No. | Sensor | Measurement | Applications |
|---|---|---|---|
| 1 | Electroencephalogram (EEG) | Frontal Lobe Activity | For emotion, problem solving, and judgement (Anxiety disorder and ADHD) |
| 2 | Temperature & Humidity | Skin Temperature & Sweat | For body's general thermal state (Fever) |
| 3 | Accelerometer & Gyroscope | Motion & Orientation | For tremors, bradykinesia (slowness of movement), and other motor symptoms (Epilepsy & Parkinson's Disease) |
| 4 | Acoustic | Body Sound | For snoring or breathing patterns (Sleep Apnea) |
| 5 | Piezoelectric (Pressure) | Forehead Muscle Tension | For stress or discomfort (Parkinson's disease and Multiple Sclerosis) |

FIG. 7

| Sl. No. | Sensors | Neurological Disorders | | | |
|---|---|---|---|---|---|
| | | Epilepsy | Parkinson's | Sleep Apnea | Stress & Anxiety |
| 1 | EEG | Detects | Detects | Detects | Detects |
| 2 | Temperature | | Detects | Detects | Detects |
| 3 | Humidity | | | Detects | |
| 4 | Accelerometer | Detects | Detects | | Detects |
| 5 | Gyroscope | Detects | Detects | | Detects |
| 6 | Acoustic | | | Detects | |
| 7 | Piezoelectric | | Detects | Detects | |

FIG. 8

WEARABLE MULTI-MODAL SENSING DEVICE FOR REAL-TIME NEUROLOGICAL MONITORING AND DISORDER DETECTION

FIELD OF THE INVENTION

The invention relates to wearable devices incorporating multi-modal sensors for real-time monitoring, analysis, and detection of neurological disorders in diverse environments.

BACKGROUND OF THE INVENTION

Neurological disorders, such as epilepsy, Parkinson's disease, and sleep apnea, affect millions worldwide, significantly impacting quality of life and requiring timely diagnosis and management. Current monitoring solutions, like electroencephalogram (EEG) systems, are often bulky, expensive, and require expert analysis, making them inaccessible for many, especially in remote or resource-limited settings. These limitations highlight the urgent need for portable, cost-effective, and user-friendly diagnostic tools.

Existing devices primarily rely on single-sensor technologies, limiting their ability to provide comprehensive neurological assessments. Multi-sensor systems exist but are prohibitively expensive or cumbersome for everyday use. Additionally, these systems often lack flexibility, adaptability, and the ability to function effectively outside clinical environments. This gap underscores the necessity of a wearable solution that integrates advanced sensing technologies for accurate, real-time monitoring.

The invention addresses these challenges by incorporating proven, low-cost, multi-modal sensors capable of detecting various neurological parameters, such as EEG activity, body temperature, motion, and acoustic signals. Designed for comfort and versatility, the wearable device can be customized to fit different body parts, enabling continuous, non-invasive monitoring of neurological health in real-world scenarios.

By leveraging advancements in sensing and data analysis technologies, this invention provides a scalable, accessible solution for individuals, healthcare professionals, and organizations. It bridges the gap between complex clinical systems and the growing demand for portable, affordable health monitoring tools, paving the way for improved management of neurological disorders globally.

BRIEF DESCRIPTION OF THE INVENTION

Aspects and advantages of the invention will be set forth in part in the following description, or may be obvious from the description, or may be learned through practice of the invention.

In one embodiment, the invention comprises a wearable, multi-modal sensing device that integrates various sensors, including EEG, temperature, humidity, accelerometer, gyroscope, piezoelectric, and acoustic sensors. The device is designed to be worn comfortably as a headband or other adaptable form factors, enabling real-time monitoring of neurological health. It utilizes advanced algorithms to analyze sensor data and identify patterns associated with neurological disorders such as epilepsy, Parkinson's disease, sleep apnea, and stress-related conditions. The device processes and displays the data on connected devices like smartphones or computers, facilitating real-time feedback and enabling users to take informed actions. Its modular design allows users to add or remove sensors depending on specific monitoring needs, providing versatility and customization for both individual and professional use.

In another embodiment, the device incorporates wireless connectivity, enabling data transmission to cloud-based systems for remote storage, diagnostics, and sharing with healthcare professionals. This feature is particularly beneficial for remote environments where access to specialized healthcare is limited. The invention's design accommodates alternative power sources, including rechargeable batteries or renewable energy options like solar power, ensuring usability in diverse settings. Additionally, the device's form factor can be adapted for other body parts, such as wrists or ankles, to meet different monitoring requirements. By offering low-cost, portable, and non-invasive solutions, this invention addresses critical challenges in neurological health monitoring, empowering individuals and healthcare professionals to improve the early detection and management of neurological disorders.

These and other features, aspects and advantages of the present invention will become better understood with reference to the following description and appended claims. The accompanying drawings, which are incorporated in and constitute a part of this specification, illustrate embodiments of the invention and, together with the description, serve to explain the principles of the invention.

BRIEF DESCRIPTION OF THE DRAWINGS

A full and enabling disclosure of the present invention, including the best mode thereof, directed to one of ordinary skill in the art, is set forth in the specification, which makes reference to the appended figures, in which:

FIG. 7 provides the list of sensors used, its measurements and their applications in accordance with embodiments of the present disclosure;

FIG. 8 provides the list of sensors and its detection of various neurological disorders in accordance with embodiments of the present disclosure;

DETAILED DESCRIPTION OF THE INVENTION

Figure 1:
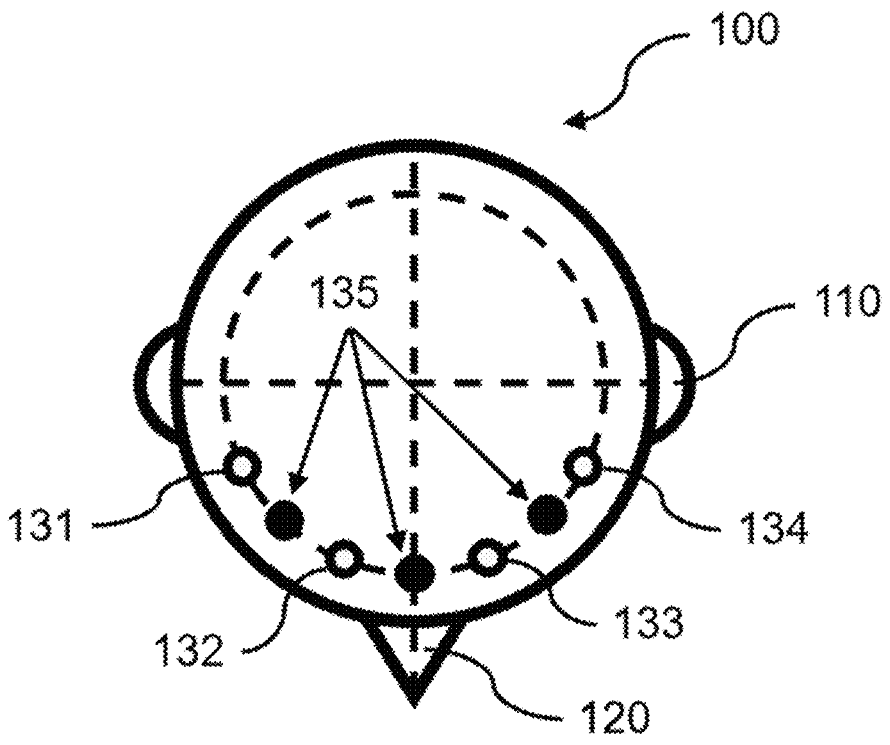
FIG. 1 provides a top view of a human head with the location of various sensors in accordance with embodiments of the present disclosure.
Figure 2:
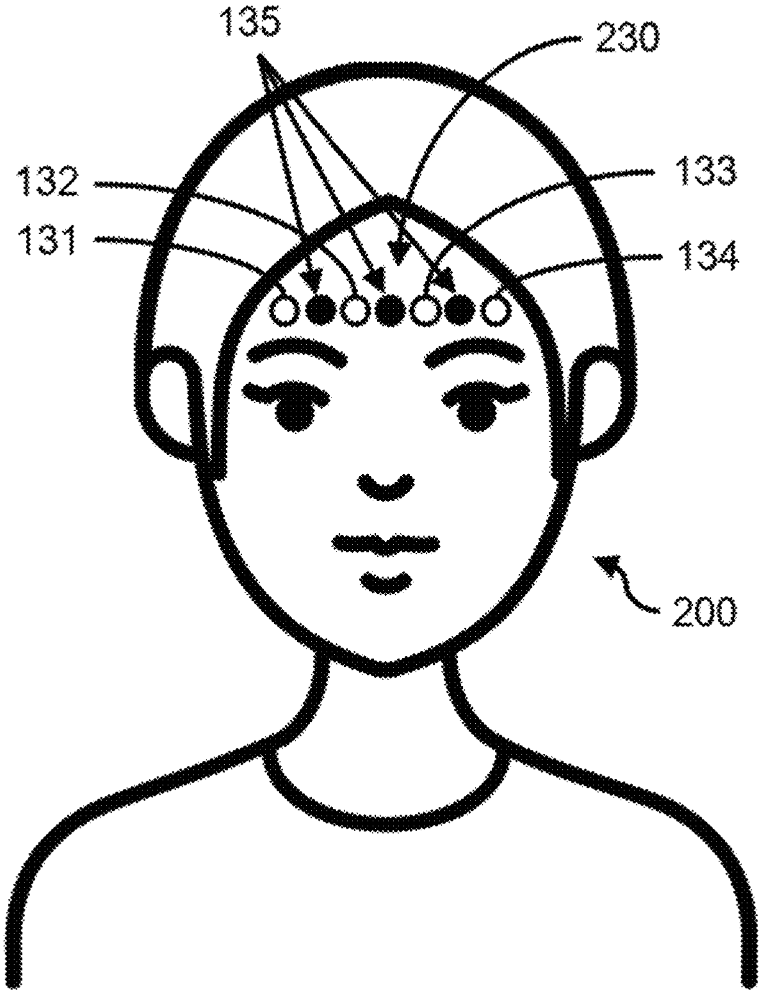
FIG. 2 provides a front view of a human head with the location of various sensors on the forehead in accordance with embodiments of the present disclosure.

Reference now will be made in detail to embodiments of the invention, one or more examples of which are illustrated in the drawings. Each example is provided by way of explanation of the invention, not limitation of the invention. In fact, it will be apparent to those skilled in the art that various modifications and variations can be made in the present invention without departing from the scope or spirit of the invention. For instance, features illustrated or described as part of one embodiment can be used with another embodiment to yield a still further embodiment. Thus, it is intended that the present invention covers such modifications and variations as come within the scope of the appended claims and their equivalents.

Figure 3:
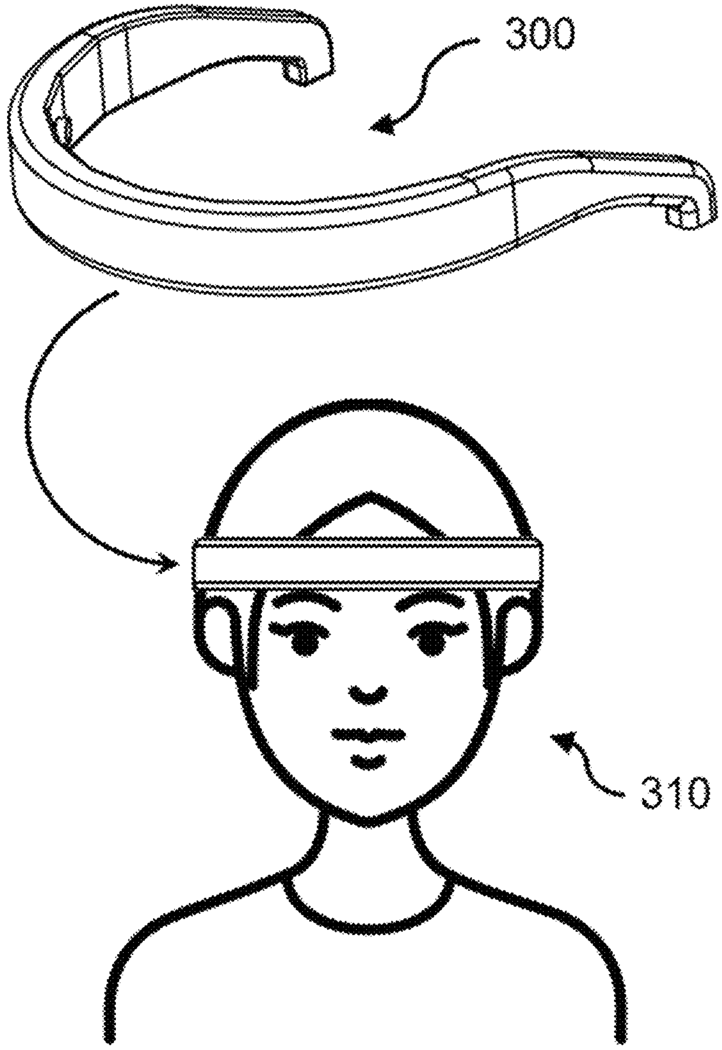
FIG. 3 provides a perspective view of the headband and a human wearing the headband in accordance with embodiments of the present disclosure.
Figure 4:
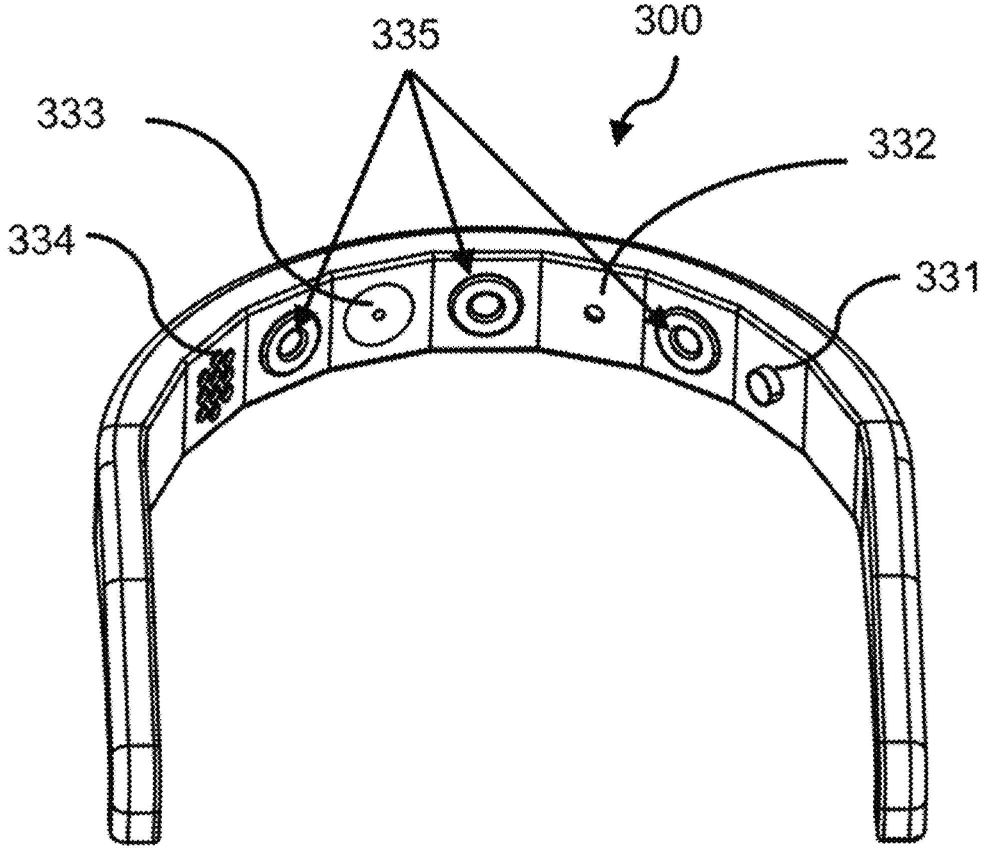
FIG. 4 provides a detailed view of the inner side of the headband with the location of various sensors and the constructional details in accordance with embodiments of the present disclosure.
Figure 5:
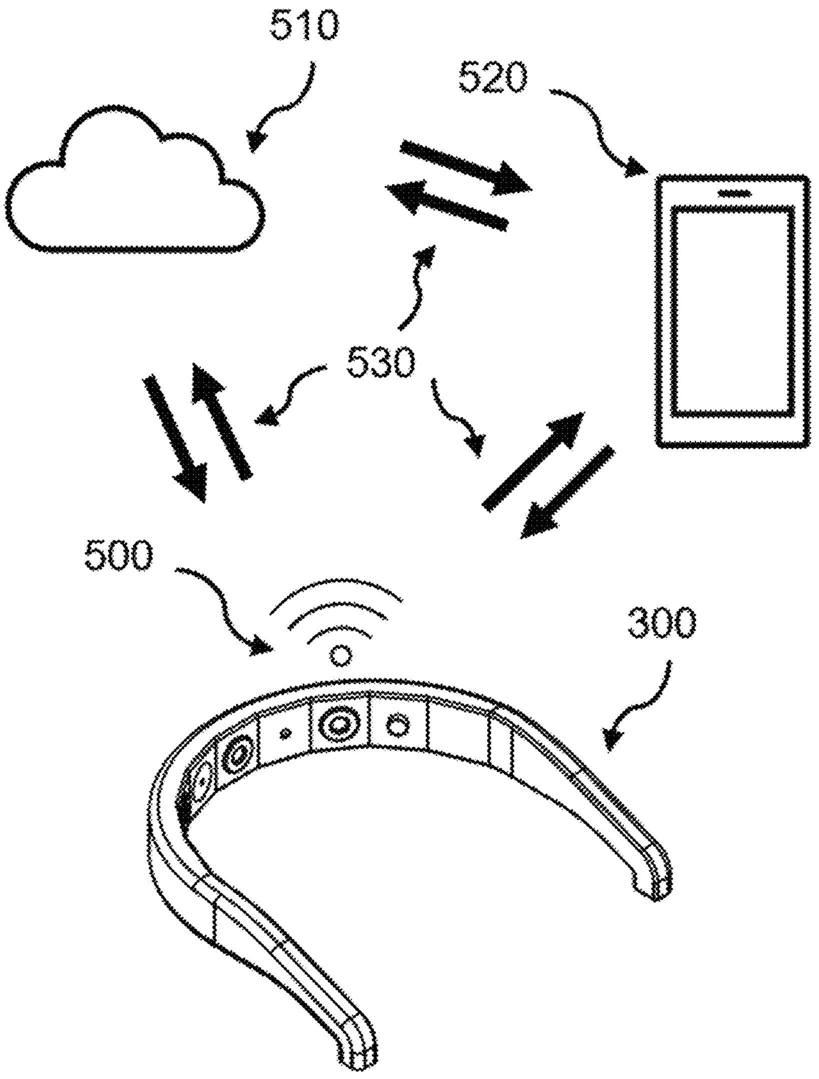
FIG. 5 provides a data communication system for the headband in accordance with embodiments of the present disclosure.

The wearable device 300, as shown in FIGS. 3, 4 and 5, is designed to monitor neurological disorders using multi-modal sensing technologies. It includes various sensors strategically placed to detect physiological parameters. The sensors include an EEG sensor 135, temperature and humidity sensors 134, accelerometer and gyroscope sensors 133, piezoelectric sensors 132, and acoustic sensors 131. These sensors are positioned on a headband to optimize signal accuracy and comfort, as illustrated in FIG. 3.

The headband 300 is constructed to ensure flexibility and adaptability. FIG. 4 depicts the inner side of the headband, where the sensors are embedded. Each sensor is mounted in specific locations, such as the forehead 230, to ensure optimal detection of signals. The band itself can be manufactured from materials like plastic, rubber, or metal, as detailed in the features document, to ensure durability and comfort for extended use.

FIG. 7 lists the types of sensors integrated into the device and their respective functions. For instance, the EEG sensor 135 detects brainwave activity to monitor conditions like epilepsy and stress. The temperature and humidity sensors 134 measure thermal states and sweat levels, aiding in detecting stress and fever. The accelerometer and gyroscope sensors 133 analyze motion and orientation, identifying tremors or other motor abnormalities such as those seen in Parkinson's disease. The piezoelectric sensors 132 measure muscle tension, while the acoustic sensors 131 detect breathing patterns for conditions like sleep apnea.

The device is equipped with a data communication system, as shown in FIG. 5, enabling wireless transmission via Wi-Fi, Bluetooth, or SIM card technology. The data is processed and stored either locally or on cloud platforms 510 for remote diagnostics and sharing with healthcare professionals. This enhances the usability of the device in remote and resource-constrained environments.

Figure 6:
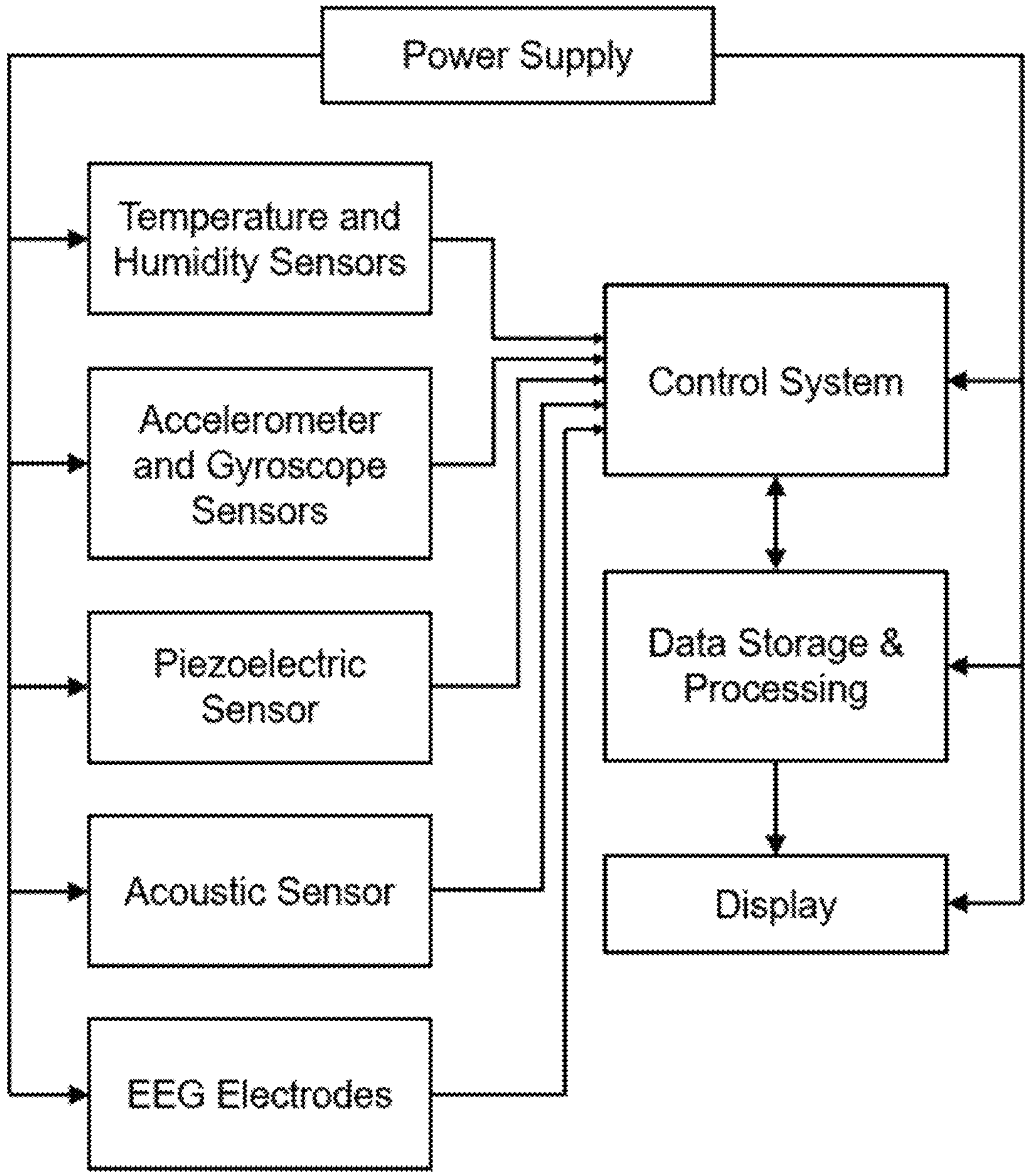
FIG. 6 provides the electrical control system block diagram of the headband in accordance with embodiments of the present disclosure.

The electrical system of the headband is detailed in FIG. 6, which includes a power supply, a control system, data storage and processing modules, and a display interface. The system integrates algorithms to analyze sensor data in real-time, providing immediate feedback on neurological health.

Figure 9:
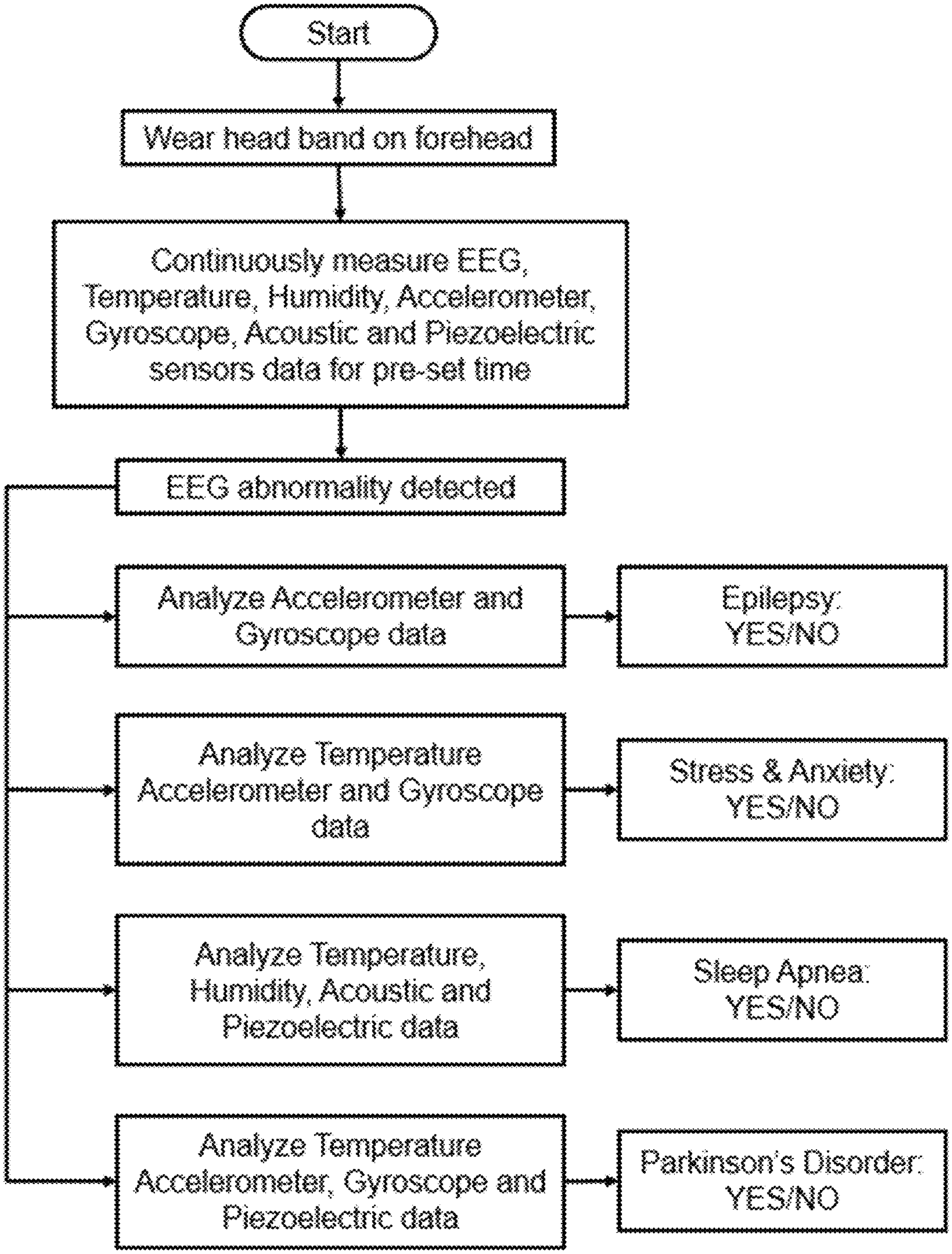
FIG. 9 provides an algorithm flow chart for the possible detection of various neurological disorders using multi-sensors in accordance with embodiments of the present disclosure.

FIG. 9 illustrates the algorithm flowchart used for detecting various neurological disorders. Sensor data is continuously collected, and abnormal patterns are flagged for further analysis. For instance, EEG abnormalities are paired with accelerometer data to detect epilepsy, while temperature and humidity levels combined with acoustic signals identify sleep apnea.

Figure 10:
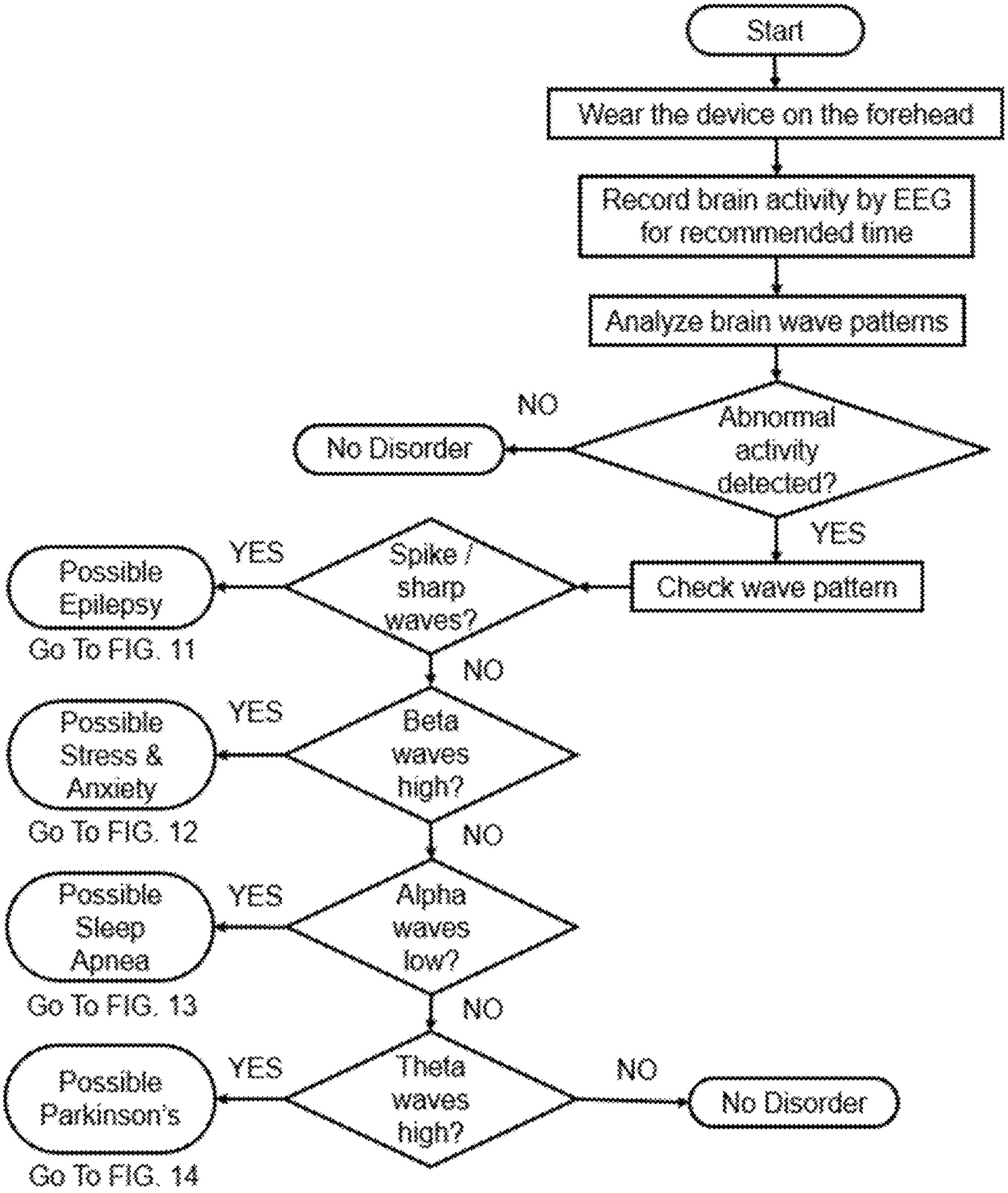
FIG. 10 provides an algorithm for EEG measurement of the headband in accordance with embodiments of the present disclosure.
Figure 11:
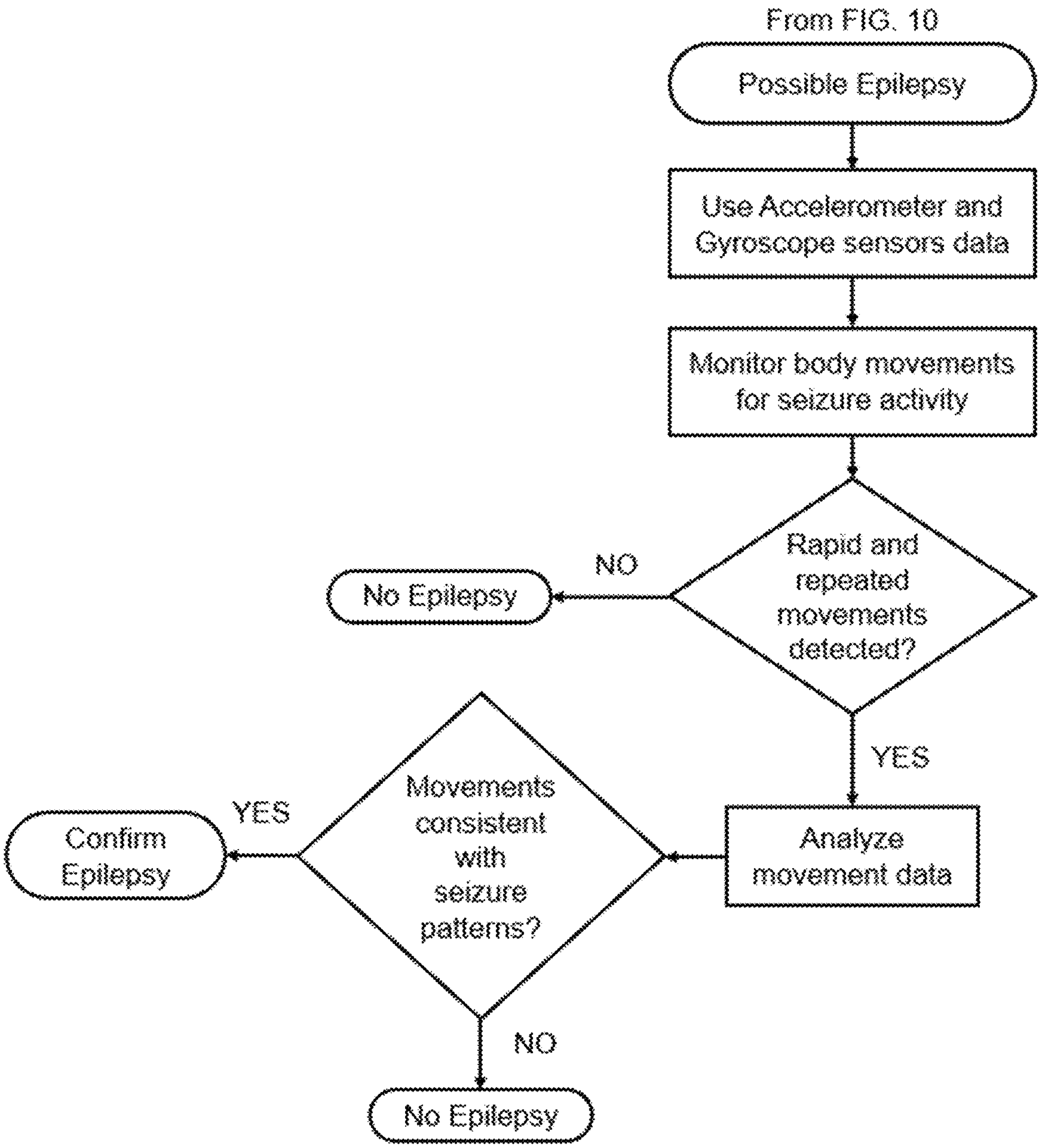
FIG. 11 provides the epilepsy algorithm for the headband in accordance with embodiments of the present disclosure.

The device incorporates specialized algorithms for EEG analysis, as shown in FIG. 10. Brainwave patterns are categorized into different types, such as beta and alpha waves, to diagnose specific conditions like stress and sleep apnea. FIG. 11 elaborates on the epilepsy detection process, which uses accelerometer data to confirm seizure activity.

Figure 12:
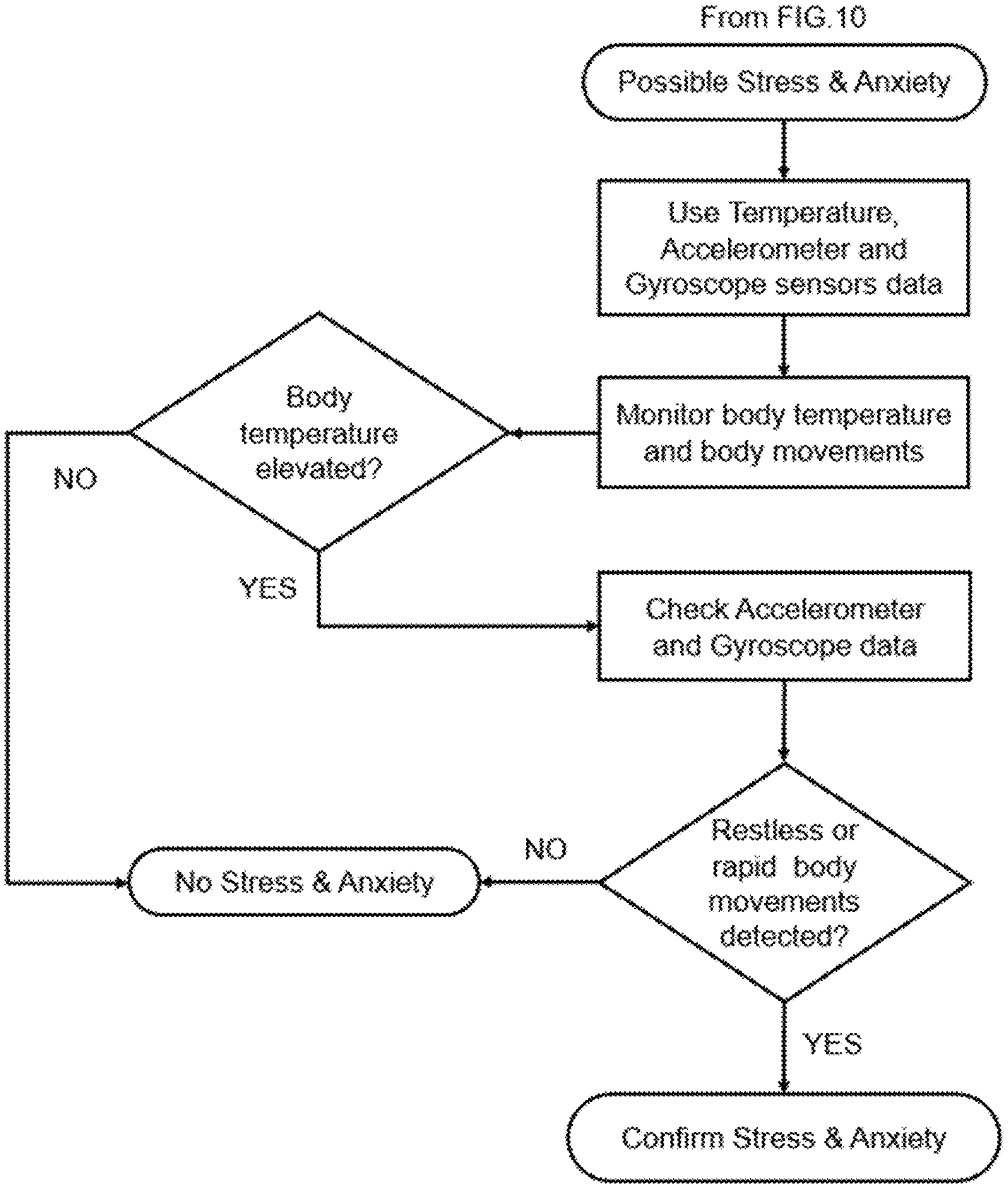
FIG. 12 provides the stress and anxiety algorithm for the headband in accordance with embodiments of the present disclosure.

The stress and anxiety detection algorithm is depicted in FIG. 12. It combines body temperature, and motion data to provide an accurate assessment of stress levels. This feature is particularly useful for managing chronic stress-related conditions.

Figure 13:
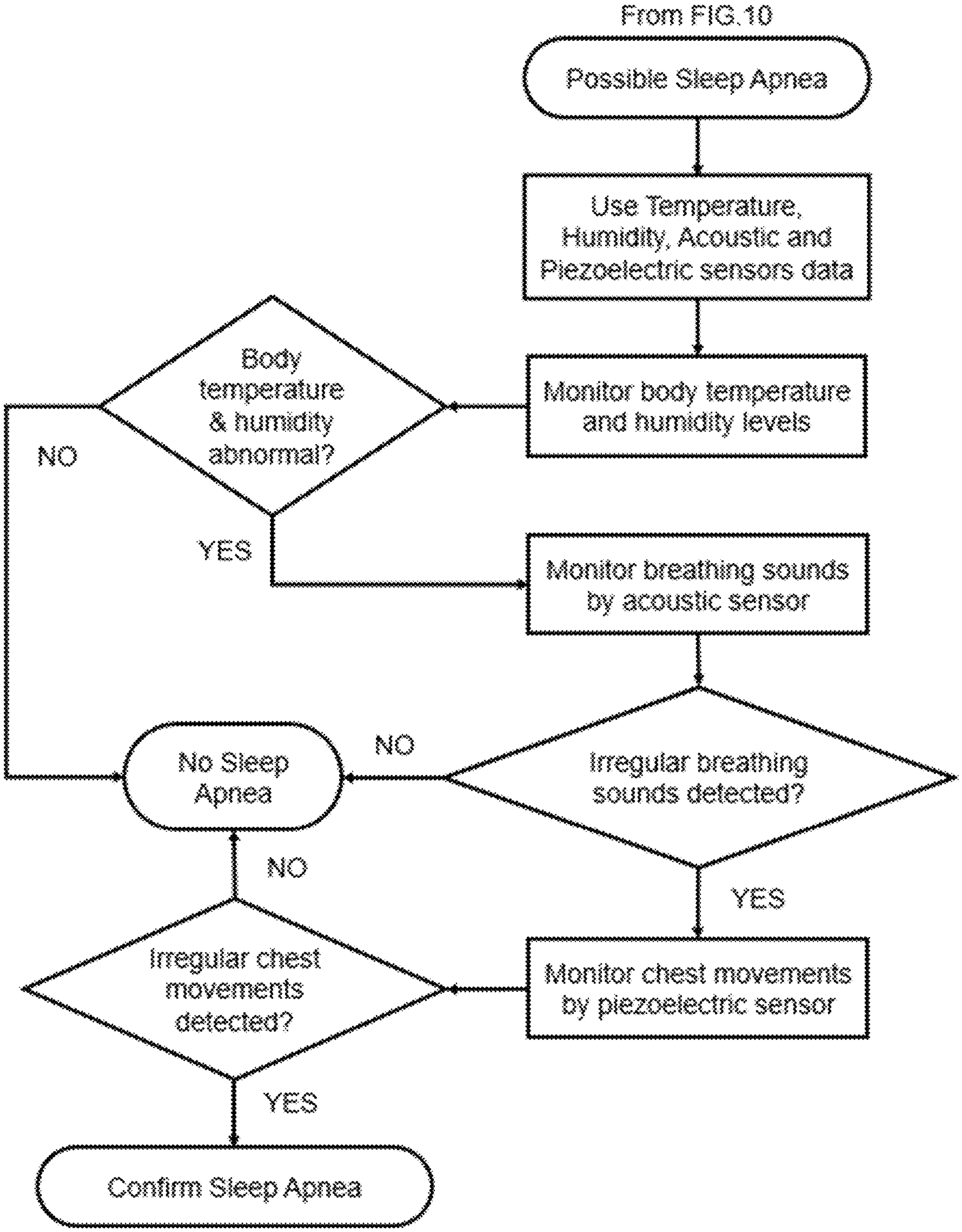
FIG. 13 provides the sleep apnea algorithm for the headband in accordance with embodiments of the present disclosure.

FIG. 13 outlines the diagnostic process for sleep apnea. Abnormal breathing patterns detected by the acoustic sensor 131 and chest movement irregularities identified by piezoelectric sensors 132 are analyzed in real-time, allowing users to monitor sleep health effectively.

Figure 14:
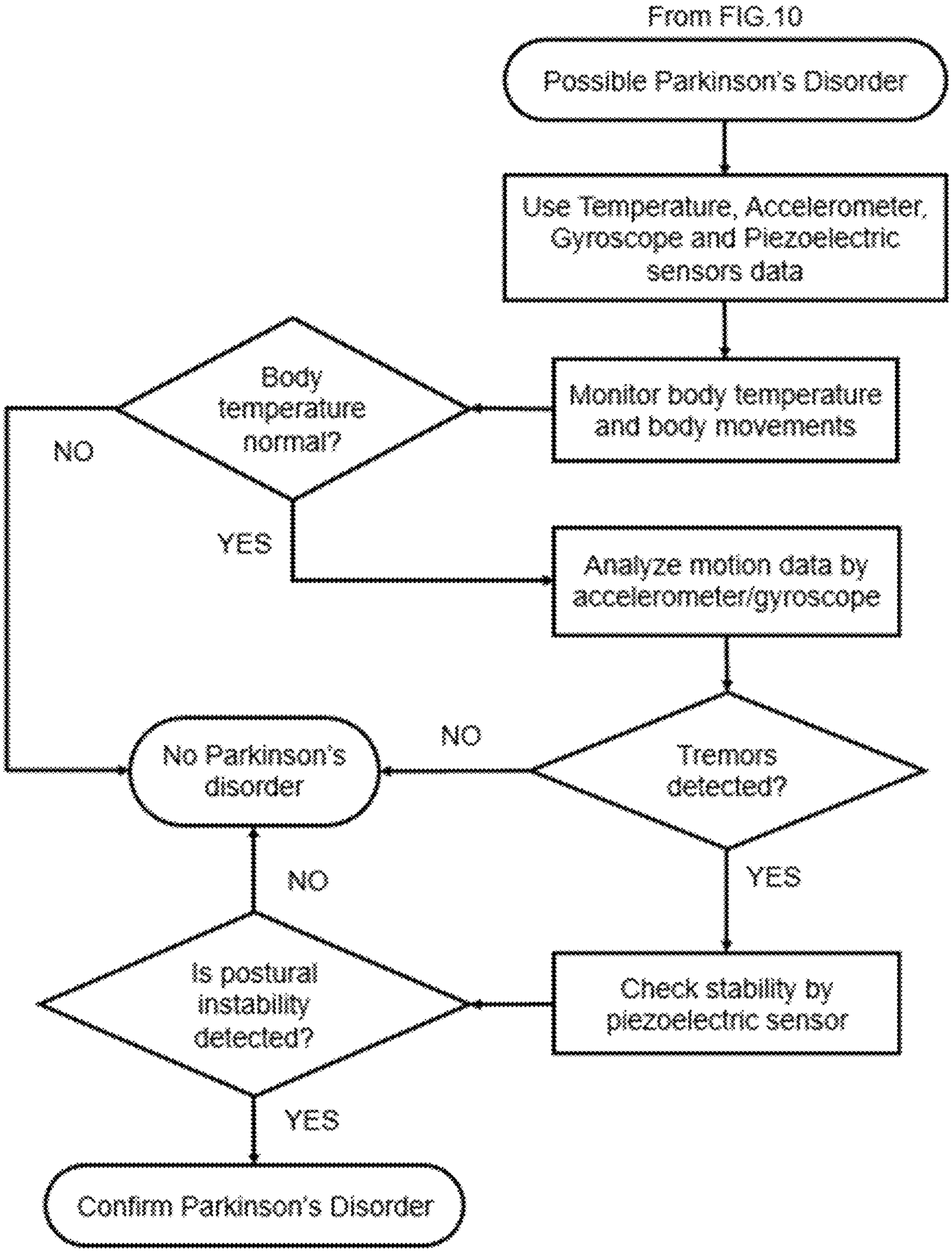
FIG. 14 provides the Parkinson's disorder algorithm for the headband in accordance with embodiments of the present disclosure.

The algorithm for Parkinson's disease diagnosis is shown in FIG. 14. Tremors and postural instability are detected using accelerometer and piezoelectric sensors, offering a non-invasive way to track motor symptoms over time.

The device features real-time feedback mechanisms, displaying results on a connected mobile application or computer interface. FIG. 5 illustrates how this connectivity is established, enabling users and healthcare providers to access and analyze data remotely.

The modular design of the headband allows users to customize the device by adding or removing sensors based on specific needs. For example, acoustic sensors can be excluded for users only interested in monitoring motor-related disorders.

The device supports various power sources, including rechargeable batteries and renewable energy options such as solar panels. This ensures usability in diverse environments, including remote areas without consistent electricity.

The headband can be constructed using rigid, flexible, or semi-flexible materials to suit different user preferences. This adaptability ensures comfort and functionality, even for extended periods of wear.

The wearable device can also be incorporated into other wearable forms, such as wristwatches or anklets, expanding its applications beyond headband usage. This versatility makes the device accessible for various demographic groups, including children and adults.

Multiple prototypes of the device, demonstrate its functionality and effectiveness. The first prototype was wired and tested for basic functionality, while the final prototype was wireless and fully operational, showcasing its advanced capabilities.

The device incorporates secure data encryption for transmitting and storing sensitive health information. This ensures user privacy and compliance with healthcare regulations.

The device is designed for both clinical and non-clinical environments. It can be used by healthcare professionals for diagnostic purposes or by individuals for daily health monitoring, bridging the gap between advanced medical equipment and everyday usability.

The device is scalable for mass production and can be manufactured using cost-effective materials and processes. This ensures affordability, making it accessible to a broader population.

The device supports remote diagnostics, enabling health-care providers to monitor patients in real-time and offer timely interventions. This feature is particularly valuable in rural and underserved areas.

Additional features, such as integrating cameras or advanced AI algorithms, can further enhance the device's diagnostic capabilities, making it a comprehensive solution for neurological health monitoring.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they include structural elements that do not differ from the literal language of the claims, or if they include equivalent structural elements with insubstantial differences from the literal languages of the claims.

DESCRIPTION OF PART NUMBERS IN THE DRAWINGS

100—Human head top view
110—Human ear
120—Human nose
131—Acoustics sensor
132—Piezoelectric or pressure sensor
133—Accelerometer and gyroscope sensors
134—Temperature and humidity sensors
135—Electroencephalogram (EEG) sensor
200—Human face
230—Human forehead
300—Headband
310—Human wearing headband
331—Acoustics sensor location
332—Piezoelectric or pressure sensor location
333—Accelerometer and gyroscope sensors location
334—Temperature and humidity sensors location
335—Electroencephalogram (EEG) sensors location
500—Wi-Fi or Bluetooth or SIM card communication
510—Cloud
520—Mobile phone
530—Two-way communication

What is claimed is:

1. A wearable neurological monitoring device comprising:

a modular structure configured as a headband for placement on a human forehead;

a plurality of physiological sensors configured to detect signals associated with neurological conditions, the plurality of physiological sensors comprising an EEG sensor, an accelerometer, a gyroscope, a temperature sensor, a humidity sensor, a piezoelectric sensor, and an acoustic sensor;

a processing unit integrated into the modular structure, the processing unit configured to:

collect signals from the plurality of physiological sensors;

integrate and analyze the collected signals using pre-defined multi-sensor algorithms to identify patterns indicative of specific neurological conditions; and generate diagnostic outputs based on the analysis;

record brain activity using the EEG sensor;

analyze brain-wave patterns in the recorded brain activity;

determine whether abnormal EEG activity is detected;

in response to detecting abnormal EEG activity, check the brain-wave patterns for spike or sharp waves;

identify possible epilepsy when the spike or sharp waves are detected;

only in response to identifying possible epilepsy based on the spike or sharp waves, use data from the accelerometer and the gyroscope to monitor body movements for seizure activity;

determine whether rapid and repeated movements are detected;

when rapid and repeated movements are detected, analyze movement data from the accelerometer and the gyroscope to determine whether the movements are consistent with seizure patterns;

generate a diagnostic output indicating confirmed epilepsy only when both the spike or sharp waves are detected and the movements are determined to be consistent with the seizure patterns; and generate a diagnostic output indicating no epilepsy when rapid and repeated movements are not detected or when the movements are determined not to be consistent with the seizure patterns;

a communication system operably connected to the processing unit, the communication system configured to wirelessly transmit the diagnostic outputs to external devices for real-time monitoring and further analysis;

wherein the device further comprises a modular sensor interface allowing for the addition or removal of sensors without disrupting device functionality, enabling customization for monitoring specific neurological conditions.

2. The device of claim 1, wherein the processing unit is configured to initiate analysis of the accelerometer and gyroscope data only after the EEG brain-wave analysis identifies the spike or sharp waves as possible epilepsy, and wherein the processing unit does not generate the diagnostic output indicating confirmed epilepsy unless both (i) the spike or sharp waves are detected and (ii) the accelerometer-and-gyroscope analysis determines that rapid and repeated movements are consistent with the seizure patterns.

3. The device of claim 1, wherein the headband is adjustable to accommodate various head sizes and shapes.

4. The device of claim 1, further comprising a mobile application operable to display real-time diagnostic outputs, send alerts, wherein at least one alert is generated in response to the diagnostic output indicating confirmed epilepsy.

5. The device of claim 1, wherein the communication system supports Wi-Fi, Bluetooth, and cellular network connectivity, and is configured to transmit the diagnostic output indicating confirmed epilepsy.

6. The device of claim 1, further comprising a cloud-based platform for storing and analyzing data remotely, with access permissions for healthcare professionals.

7. The device of claim 1, wherein the diagnostic outputs include visual, auditory, or haptic feedback to alert users of the diagnostic output indicating confirmed epilepsy.

8. The device of claim 1, wherein the processing unit is configured to execute algorithms for detecting epilepsy, Parkinson's disease, sleep apnea, stress, and anxiety disorders wherein, when abnormal EEG activity is detected, the processing unit is further configured to evaluate the brain-wave patterns in a sequence comprising: checking for spike or sharp waves and identifying possible epilepsy when the spike or sharp waves are detected; when the spike or sharp waves are not detected, determining whether beta waves are high and identifying possible stress or anxiety when the beta waves are high; when the beta waves are not high, determining whether alpha waves are low and identifying possible sleep apnea when the alpha waves are low; when the alpha waves are not low, determining whether theta waves are high and identifying possible Parkinson's disease when the theta waves are high; and identifying no disorder when the theta waves are not high.

9. The device of claim 1, wherein the processing unit is configured to generate a diagnostic output indicating no disorder when abnormal EEG activity is not detected, and to generate the diagnostic output indicating no epilepsy when possible epilepsy is identified from the EEG brain-wave analysis but either rapid and repeated movements are not detected or the analyzed movements are not consistent with the seizure patterns.

* * * * *